United States Patent [19]

Albright et al.

[11] 4,282,142
[45] Aug. 4, 1981

[54] FLAME-RETARDED POLYOLEFIN POLYMERIC COMPOSITIONS CONTAINING 3,9-BROMOPHENOXY-2,3,8,10-TETRAOXA-3,9-DIPHOSPHASPIRO (5.5)UNDECANE-3,9-DIOXIDES

[75] Inventors: James A. Albright, Hampton, N.J.; Chester J. Kmiec, Williamsville, N.Y.

[73] Assignee: Velsicol Chemical Corporation, Chicago, Ill.

[21] Appl. No.: 130,312

[22] Filed: Mar. 14, 1980

Related U.S. Application Data

[60] Division of Ser. No. 33,601, Apr. 27, 1979, Pat. No. 4,226,813, which is a continuation-in-part of Ser. No. 685,754, May 13, 1976, abandoned.

[51] Int. Cl.³ .................. C07F 9/15; C08K 5/52
[52] U.S. Cl. ................. 260/45.7 P; 260/45.75 B; 260/45.8 R
[58] Field of Search .......... 260/45.8 R, 927 R, 45.7 P

[56] References Cited

U.S. PATENT DOCUMENTS

| | | | |
|---|---|---|---|
| 3,090,799 | 5/1963 | Wahl et al. | 260/927 R |
| 3,557,053 | 1/1971 | Miller | 260/45.7 P |
| 3,866,405 | 2/1975 | Knopka | 260/45.7 P |
| 3,978,167 | 8/1976 | Albright | 260/45.8 R |
| 4,143,101 | 3/1979 | Mayerhoefer et al. | 260/45.8 R |

OTHER PUBLICATIONS

Hilado, Flammability Handbook for Plastics, 1969, pp. 82-86.

Primary Examiner—Howard E. Schain
Assistant Examiner—R. A. White
Attorney, Agent, or Firm—Dietmar H. Olesch; Robert J. Schwarz

[57] ABSTRACT

A flame retarded polyolefin polymer containing from about 1 to about 40 percent (by combined weight of polymer and flame retardant) of the compound of the formula

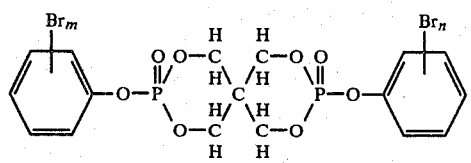

wherein m and n are integers independently selected from the group consisting of 2, 3, 4, and m plus n equal 6.

6 Claims, No Drawings

FLAME-RETARDED POLYOLEFIN POLYMERIC COMPOSITIONS CONTAINING 3,9-BROMOPHENOXY-2,3,8,10-TETRAOXA-3,9-DIPHOSPHASPIRO (5.5)UNDECANE-3,9-DIOXIDES

This is a division of the copending application of Ser. No. 33,601 filed Apr. 27, 1979, now U.S. Pat. No. 4,226,813, which is a continuation-in-part of the copending application, Ser. No. 685,754, which was filed on May 13, 1976 now abandoned.

FIELD OF THE INVENTION

A 3,9-bromophenoxy-2,4,8,10-tetraoxa-3,9-diphosphaspiro(5.5)-undecane-3,9-dioxide and a flame-retarded polyolefin resin containing said dioxide.

DESCRIPTION OF THE PRIOR ART

U.S. Pat. No. 3,090,799 of Wahl and Grabhofer discloses plasticizers of the formula

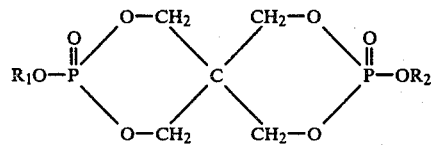

wherein . . . $R_1$ and $R_2$ represent aliphatic, cycloaliphatic, heterocyclic or aromatic radicals, the hydrogen atoms of which can be substituted, for example, by halogen, ester, keto, nitrile, or amino groups. Millions of compounds are "described" by the formula of Wahl et al.; many of them are substantially ineffective in imparting flame retardancy to polyolefin polymers.

Applicants have discovered that a limited class of 3,9-bromophenoxy-2,4,8,10-tetraoxa-3,9-diphosphar-spiro(5.5)undecane-3,9-dioxide compounds unexpectedly impart a high level of flame retardancy to polyolefin polymers.

SUMMARY OF THE INVENTION

In accordance with this invention, there is provided a compound of the formula

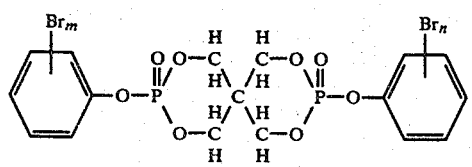

wherein m and n are integers independently selected from the group consisting of 1,2,3,4, and m plus n equal 6.

DESCRIPTION OF THE PREFERRED EMBODIMENTS

The compound of this invention is of the formula

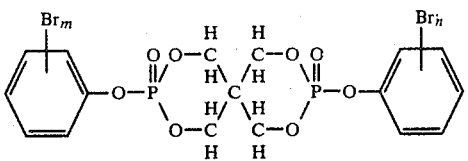

wherein m and n are integers independently selected from the group consisting of 1,2,3,4, and m plus n equal 6. In a preferred embodiment, both m and n are 3.

The compound of this invention may be prepared by reacting a 3,9-dihalo-2,4,8,10-tetraoxa-3,9-diphosphaspiro(5.5)undecane-3,9-dioxide with substituted halophenols to yield the appropriate diphosphate ester. Alternatively, one may use the metal salts of the halophenol. The reaction can be carried out by simply mixing the halophosphate and the halophenol or halophenol metal salt reactants together and heating the mixture gently at a temperature of 30° to 160° C. from 1 to 12 hours. The above reaction can be conducted in the presence or absence of inert solvents. Suitable inert solvents include aromatic solvents such as, e.g., benzene, toluene, dipolar aprotic solvents such as, e.g., dimethylforamide, dimethylsulfoxide, acetonitrile; and the like. Catalytic quantities of a metal salt or oxide, such as magnesium oxide, magnesium chloride, calcium oxide, calcium chloride, titanium chloride, or vanadium acetate may be used or one may use stochiometric quantities of a weak organic base (such as pyridine or triethylamine) to accelerate the completion of the reaction. The halophosphate starting reactant can be prepared by reacting pentaerythritol with a phosphorus oxyhalide.

The compounds within the scope of this invention can also be prepared according to the following reaction scheme:

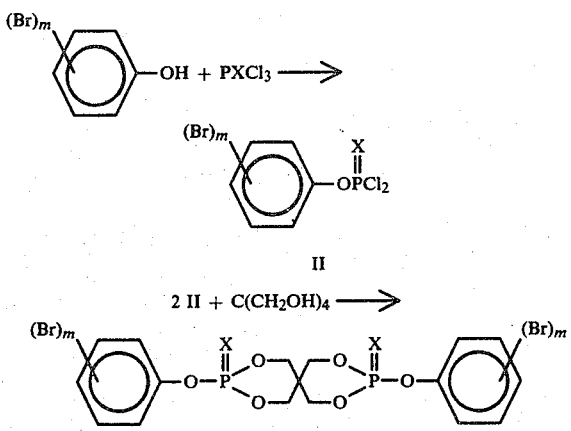

The flame retardants within the scope of this invention as well as mixtures thereof display an unobvious level of flame retardant efficacy in polyolefin polymeric compositions. Exemplary polyolefin polymers with which the flame retardants of this invention may be combined include homopolymers of ethylene, propylene, butene, and hexane and copolymers of two or more monomers, e.g., ethylene/propylene copolymers, ethylene/butene copolymers, and ethylene/hexene copolymers. A preferred class of polyolefin polymers which can be used with the flame retardants of this invention are propylene homo- and copolymers. A further description of polyolefin polymers capable of being used in this invention can be found in Modern Plastics Encyclopedia, Vol. 52, No. 10A, McGraw-Hill, Inc., New York, New York (1975), and the Encyclopedia of Polymer Science and Technology, Interscience Publishers, John Wiley & Sons, New York, N.Y. (Vol. 2, Butylene Polymers-1965; Vol. 6, Ethylene Polymers-1967 and Vol. 11, Propylene Polymers-1969), said publications being incorporated herein in toto by reference.

The flame retardants of this invention can be incorporated into or applied onto flammable polyolefin polymeric material by techniques which are known to those skilled in the art. See, for example, J. M. Lyons, "The Chemistry and Uses of Fire Retardants," Wiley-Interscience, New York, 1970, and Z. E. Jolles, "Bromine and Its Compounds," Academic Press, New York, 1966. Depending on the substrate and the amount of flame retardancy desired, from about 1 to about 40 weight percent of the flame retardant compound can be incorporated therewith. However, in most applications it is preferred to use from 1 to about 25 weight percent of said compounds. It should be noted that the optimum level of additive of the flame retardant within the scope of this invention depends upon the particular substrate being treated as well as the level of flame retardancy desired. For example, in polypropylene a flame retardant load level of from about 5 to about 25 percent by weight of the total polymeric composition is satisfactory.

In addition to the flame retardant compounds within the scope of this invention, the flame retardancy of a polymer can be further modified through the use of so-called "synergists" or enhancing agents, although preferably no synergist or enhancing agent is used with the flame retardant phosphates of this invention. These "enhancing agents" comprise the oxides and halides of groups IVA and VA of the Periodic Table, and are further described in Modern Plastics Encyclopedia, ibid., as well as U.S. Pat. Nos. 2,993,924; 2,996,528; 3,205,196 and 3,878,165. Without limitation, preferred enhancing agents include $Sb_2O_3$, $SbCl_3$, $SbBr_3$, $SbI_3$, SbOCl, $As_2O_3$, $As_2O_5$, $ZnBO_4$, $BaB_2O_4.H_2O$, $2.ZnO.3-B_2O_3.3.5H_2O$ and stannous oxide hydrate. The more preferred enhancing agent is antimony trioxide.

It is also within the scope of the present invention to employ other materials in the present invention compositions where one so desired to achieve a particular end result. Such materials include, without limitation, adhesion promotors, antioxidants, antistatic agents, antimicrobials, colorants, heat stabilizers, light stabilizers, and fillers. The above mentioned materials, including filler, are more fully described in Modern Plastics Encyclopedia, ibid., which publication has been incorporated herein in toto by reference.

The amount of the above described materials employed in the present invention compositions can be any quantity which will not substantially adversely affect the desired results derived from the present invention compositions. Thus, the amount used can be zero (0) percent, based on the total weight of the composition, up to that percent at which the composition can still be classified as a plastic. In general, such amount will be from about 0% to about 75% and more specifically from about 1% to about 50%.

The following examples are provided for the purpose of further illustration only and are not intended to be limitative of the disclosed invention. Unless otherwise specified, all temperatures are expressed in degrees centigrade, all weights are expressed in grams, and all volumes are expressed in milliliters.

EXAMPLE 1

3,9-bis(2',4',6'-tribromophenoxy)-2,4,8,10-tetraoxa-3,9-diphosphaspiro(5.5)undecane-3,9-dioxide The sodium salt of tribromophenol (282 grams) was partially dissolved and suspended in one liter of acetonitrile. To this mixture, 119 grams of 3,9-dichloro-2,4,8,10-tetraoxa-3,9-diphosphaspiro(5.5)undecane-3,9-dioxide were added over a one-half hour period. A slight exotherm was noted. Upon complete addition, the mixture was stirred and heated to 70° C. for three hours. The resulting solid white mass was filtered and the product washed thoroughly with two liters of warm water. The solid was subsequently washed twice with boiling acetone to yield 322 grams (81 percent) of a white solid with a melting point of 282° to 286° C. This product contained 52.06 percent of bromine.

COMPARATIVE EXAMPLE 2

3,9-bis(2',3',4',5',6'-pentabromophenoxy)-2,4,8,10-tetraoxa-3,9-diphosphaspiro(5.5)undecane-3,9-dioxide The sodium salt of pentabromophenol (460 grams) was suspended in about three liters of acetonitrile in a five-liter flask. To the above suspension were slowly added 133.7 grams (0.45 mole) of 3,9-dichloro-2,4,8,10-tetraoxa-3,9-diphosphaspiro(5.5)undecane-3,9-dioxide. The reactants were stirred for half an hour and then heated gently. An additional liter of acetonitrile was added to the reaction system, and then said system was heated up to 70° C. and held at that temperature for 2.5 hours. The system was cooled, filtered, reslurried with water, refiltered with a centrifuge, and then air dried. The dried residue was given a boiling acetone wash, filtered through a centrifuge, and then dried at 95° C. A yield of 69.7 percent (377 grams) of product was obtained. This product had a melting point of 324° to 326° C.

COMPARATIVE EXAMPLE 3

3,9-bis(2',3',4',5',6'-pentachlorophenoxy)-2,4,8,10-tetraoxa-3,9-diphosphaspiro(5.5)undecane-3,9-dioxide Pentachlorophenol (97 grams; 0.364 mole), potassium chloride (3.6 grams), and phosphorus oxychloride (447 grams) were heated to reflux in a one liter flask equipped with a magnetic stirrer. The reaction mixture was refluxed for 16 hours, cooled to room temperature, and then filtered. Excess phosphorus oxychloride was removed under vacuum. The pentachlorophenyl dichlorophosphate residue (125 grams; 0.326 moles) was dissolved in toluene. To this solution was added 22.2 grams (0.163 mole) of pentaerythritol. This reaction mixture was heated to reflux, held at the reflux temperature 2.75 hours, cooled to room temperature, and then filtered. The residue was air dried and then dried for two hours at 110° C. 117.5 grams of product were obtained in 95.3 percent yield. This product had a melting point greater than 380° C. and contained 46.44 percent of chlorine.

COMPARATIVE EXAMPLE 4

3,9-bis-(2',4',6'-trichlorophenoxy)-2,4,8,10-tetraoxa-3,9-diphosphaspiro-(5.5)undecane-3,9-dioxide The sodium salt of trichlorophenol (253 grams) was partially dissolved and suspended in one liter of acetonitrile. To this mixture, 171 grams of 3,9-dichloro-2,4,8,10-tetraoxa-3,9-diphosphaspiro(5.5)undecane-3,9-dioxide were added over a one-half hour period. A slight exotherm was noted. Upon complete addition, the mixture was stirred and heated to 70° C. for three hours. The resulting solid white mass was filtered and the product washed thoroughly with warm water. The solid was subsequently washed twice with cold acetone to yield 181 grams (51 percent) of a white solid with a melting point of 283° C. which contained 30.9 percent of chlorine.

EXAMPLE 5

3,9-bis(2',4',6'-tribromophenoxy)-2,4,8,10-tetraoxa-3,9-diphosphaspiro(5.5)undecane-3,9-dioxide was dry blended with polypropylene resin (Hercules 6823 brand of polypropylene manufactured by Hercules, Inc., Wilmington, Delaware) in a Brabended compounding machine ("Prep Center", Model R6, C. W. Brabender Instruments, Inc., Hakensack, N.J.). A 25%/75% dioxide/polypropylene concentrate was blended in this compounding machine, discharged, cooled, ground and mixed with an equal amount of resin to prepare a polypropylene resin containing 12.5 percent by weight of the dioxide. This resin was then fed into a Newbury injection molding machine (Model HI-30RS manufactured by Newbury Instruments, Inc., Newbury, Ohio); test specimens were molded using a screw speed of 250 revolutions per minute, an initial injection pressure of 2,000 pounds per square inch, internal barrel temperatures of 410 degrees fahrenheit (front zone) and 440 degrees fahrenheit (rear zone), a cycle time of 60 seconds, a total injection time of 20 seconds, and a total stroke time of 4.0 seconds.

The test specimens were tested for flammability in accordance with Underwriter's Laboratory Subject No. 94 test (U.L. Tests for Flammability of Plastic Materials, U.L. 94, Feb. 1, 1974). In this test, the test specimen was supported from the upper end, with the longest dimension vertical, by a clamp on a ring stand so that the lower end of the specimen was ⅜" above the top of the burner tube. The burner was then placed remote from the sample, ignited, and adjusted to produce a blue flame ¾" in height. The test flame was placed centrally under the lower end of the test specimen and allowed to remain for 10 seconds. The test flame was then withdrawn, and the duration of flaming or glowing combustion of the specimen was noted. If flaming or glowing combustion of the specimen ceased within 30 seconds after removal of the test flame, the test flame was again placed under the specimen for 10 seconds immediately after flaming or glowing combustion of the specimen stopped. The test flame was again withdrawn, and the duration of flaming or glowing combustion of the specimen was noted. If the specimen dripped flaming particles or droplets while burning in this test, these drippings were allowed to fall onto a horizontal layer of cotton fibers (untreated surgical cotton) placed one foot below the test specimen. Significantly flaming particles were considered to be those capable of igniting the cotton fibers. The duration of flaming or glowing combustion of vertical specimens after application of the test flame (average of 5 specimens with 10 flame applications) should not exceed 25 seconds (maximum not more than 30 seconds) and the portion of the specimen outside the clamp should not be completely burned in the test.

Materials which complied with the above requirements and did not drip any flaming particles or droplets during the burning test were classified as "V-1". Materials which complied with the above requirement but dripped flaming particles or droplets which burned briefly during the test were classified as "V-2". A "V-0" rating was given to materials wherein the duration of flaming or glowing combustion averaged less than five seconds under the conditions specified above.

The flame-retarded polypropylene composition of this example had a U.L. 94⅛" rating of V-0.

COMPARATIVE EXAMPLES 6-8

In substantial accordance with the procedure of Example 5, samples of Hercules 6823 polypropylene resin containing flame retardants outside of the scope of the claims of this application were prepared and tested. Table I indicates the amount and type of flame retardant in each of the polypropylene samples tested and the U.L. 94⅛" rating obtained.

TABLE I

| Example No. | Flame Retardant | Concentration of Flame Retardant (By Weight) | U.L. 94 ⅛" Rating |
|---|---|---|---|
| 5 | 3,9-bis(2',4',6'-tribromophenoxy)-2,4,8,10-tetraoxa,3,9-diphosphaspiro(5.5)undecane-3,9-dioxide | 12.5 | V-O |
| 6 | 3,9-bis(2',3',4',5',6'-pentabromophenoxy)-2,4,8,10-tetraoxa-3,9-diphosphaspiro(5.5)undecane-3,9-dioxide | 12.5 | HB |
| 7 | 3,9-bis(2',3',4',5',6'-pentachlorophenoxy)-2,4,8,10-tetraoxa-3,9-diphosphaspiro(5.5)undecane-3,9-dioxide | 18.0 | HB |
| 8 | 3,9-bis(2',4',6'-trichlorophenoxy)-2,4,8,10-tetraoxa-3,9-diphosphaspiro(5.5)undecane-3,9-dioxide | 12.5 | V-2 |

TABLE II

| Polymer | Flame Retardent of Example No. | Flame Retardant/Antimony Oxide Load level | O.I.[a],% | ΔO.I. |
|---|---|---|---|---|
| Base Resins: | | | | |
| Polystyrene | — | 0/0.5 phr[b] | 19 | — |
| HIPS | — | 0/0 | 18 | — |
| LDPE | — | 0/0 | 19 | — |
| Comparative Polymeric Compositions: | | | | |
| Polystyrene | 1 | 5 phr/0.5 phr[b] | 21 | 2 |
| Polystyrene | 1 | 10 phr/0.5 phr[b] | 23 | 4 |
| HIPS | 1 | 12.5%/0 | 21 | 3 |
| HIPS | 1 | 18%/0 | 22 | 4 |
| HIPS | 1 | 12%/2.4% | 20.5 | 2.5 |

TABLE II-continued

| Polymer | Flame Retardent of Example No. | Flame Retardant/Antimony Oxide Load level | O.I.[a],% | ΔO.I. |
|---|---|---|---|---|
| HIPS | 1 | 18%/3.6% | 21.5 | 3.5 |
| Polymeric Compositions of This Invention: | | | | |
| LDPE | 1 | 18%/0 | 29.5 | 10.5 |

[a]ASTM D-2863-74.
[b]Synergist used was dicumyl peroxide rather than antimony oxide.

EXAMPLE 9

A solution of 600 grams of polystyrene, 2,670 grams of methylene chloride, 60 grams of hexane, and 5 parts per hundred resin (phr) of the compound of Example 1 was prepared. To the above solution was added 3 grams of dicumyl peroxide as a flame retardant synergist. The mixture was poured into an aluminum dish, and the methylene chloride was allowed to evaporate. Following this, the casting was steamed to produce a crude foam. This foam was then cut into sufficient specimens of appropriate sizes in order to subject said foam to various tests; the data obtained therefrom are reported in Table II.

The same processing conditions were used to make additional polystyrene foam samples having different flame retardant load levels. These samples were tested in the same manner.

EXAMPLE 10

The flame retardant of Example 1 (40% of the total mixture by weight) was dry mixed with high impact polystyrene (HIPS) resin (52% by weight) and 8% by weight antimony oxide (Cosden 825 TV-K brand HIPS, Cosden Oil & Chemical Co., Big Springs, Texas). The mixture was melt blended in a Brabender "Prep Center" compounding machine at a temperature of 240° C., a mixing time of 2 to 3 minutes and from 100 to 120 revolutions per minute ("Prep-Center" brand compounding machine, C. W. Brabender Instruments, Inc., S. Hackensack, N.J.). The discharge mass was cooled, ground and let down so that it contained 18 percent flame retardant (by weight) and 3.6% antimony oxide (by weight). The resin was then injection molded using a 30-ton Newbury one ounce injection molding machine with a screw speed of 250 revolutions per minute, an initial injection pressure of 2,000 pounds per square inch, internal barrel temperatures of 440° F. (rear zone) and 470° F. (front zone), a cycle time of 60 seconds, a total injection time of 20 seconds, and a total stroke time of 5 seconds. The final HIPS polymeric composition was subjected to various tests, and the data obtained therefrom are reported in Table II.

The same processing conditions as above were used to make additional HIPS polymeric samples having different flame retardant and antimony oxide load levels. Using substantially the same injection molding conditions described above (except that the internal barrel temperature rear and front zones were 420° and 470° F., respectively), HIPS samples were also prepared with neither flame retardant additive nor antimony oxide present. The absence of the prior melt blending step and the difference in the rear and front zone internal barrel temperatures have no impact on the flame retarding efficacy of the HIPS base resin. These samples were tested in the same manner.

EXAMPLE 11

Thirty-six parts (per hundred parts by weight of total mixture) of the flame retardant of Example 1 were dry mixed with Union Carbide 3900 brand of low density polyethylene. The mixture was melt blended in a Brabender "Prep Center" compounding machine at a temperature of 220 degrees centigrade, a mixing time of 2 to 3 minutes, and 100 revolutions per minute. The discharge mass was cooled and ground. The flame retarded concentrate was dry blended with low density polyethylene resin so that the blend produced contained 18 percent (by weight) of the flame retardant of Example 1. This resin was injection molded in a 30-ton Newbury one ounce injection molding machine at a screw speed of 250 revolutions per minute, an initial injection pressure of 2,000 pounds per square inch, internal barrel temperatures of 410 degrees Fahrenheit (rear zone) and 440 degrees Fahrenheit (front zone), a cycle time of 60 seconds, a total injection time of 20 seconds, and a total stroke time of 3 seconds. The low density polyethylene samples were subjected to various tests; the test data are reported in Table II.

In substantial accordance with the procedures of this Example, additional low density polyethylene samples were prepared which did not contain any flame retardant additive. The absence of the prior melt blending step had no impact upon the flame retarding efficacy of the low density polyethylene base resin. These samples were tested in the same manner, and the results obtained are reported in Table II.

Based upon this disclosure, many other modifications and ramifications will naturally suggest themselves to those skilled in the art; they are intended to be comprehended within the scope of this invention.

We claim:

1. A flame retarded polyolefin polymer containing from about 1 to about 40 percent (by combined weight of polymer and flame retardant) of the compound of the formula

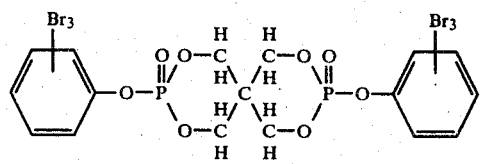

2. The polyolefin polymer of claim 1, wherein said polymer is polyethylene.

3. The polyolefin polymer of claim 1, wherein said polymer is polypropylene.

4. A method for preparing flame retarded polyolefin which comprises incorporating into the polyolefin from about 1 to about 40 weight percent of a flame retardant compound of the formula

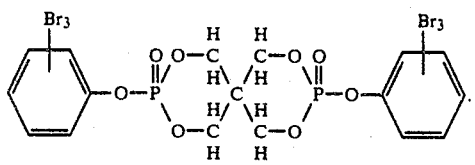
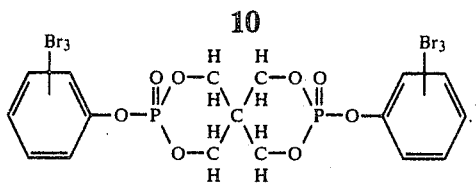
5. The method of claim 4 wherein the polyolefin is polyethylene.
6. The method of claim 4 wherein the polyolefin is polypropylene.
5. The method of claim 4 wherein the polyolefin is polyethylene.
6. The method of claim 4 wherein the polyolefin is polypropylene.

UNITED STATES PATENT AND TRADEMARK OFFICE
CERTIFICATE OF CORRECTION

PATENT NO. : 4,282,142

DATED : August 4, 1981

INVENTOR(S) : James A. Albright and Chester J. Kmiec

It is certified that error appears in the above-identified patent and that said Letters Patent are hereby corrected as shown below:

On the title page, Item [54] and
Column 1, line 5, "2,3,8,10-" should read -- 2,4,8,10- --.

Column 5, line 18 "Brabended" should read -- Brabender --.

line 20 "Hakensack" should read -- Hackensack --.

Column 6, line 41 "-3,9-dioxide" should read -- ,3,9-dioxide --.

line 51 "trichlorophenoxy)-2" should read

-- trichlorophenoxy)-2, --.

In the heading of Column 3, Table I "Retartdant" should read -- Retardant --.

Column 10 should be deleted.

Signed and Sealed this

*Fifteenth* Day of *December 1981*

[SEAL]

Attest:

GERALD J. MOSSINGHOFF

*Attesting Officer*  *Commissioner of Patents and Trademarks*